(12) United States Patent
Fox et al.

(10) Patent No.: US 8,965,071 B2
(45) Date of Patent: Feb. 24, 2015

(54) ASSESSING TUMOR RESPONSE TO THERAPY

(75) Inventors: Tim Fox, Atlanta, GA (US); Ian Crocker, Atlanta, GA (US); Paul Pantalone, Atlanta, GA (US); Eduard Schreibmann, Atlanta, GA (US)

(73) Assignee: Emory University, Atlanta, GA (US)

( * ) Notice: Subject to any disclaimer, the term of this patent is extended or adjusted under 35 U.S.C. 154(b) by 1214 days.

(21) Appl. No.: 12/130,530

(22) Filed: May 30, 2008

(65) Prior Publication Data

US 2009/0296998 A1 Dec. 3, 2009

(51) Int. Cl.
| | |
|---|---|
| G06K 9/00 | (2006.01) |
| G06K 9/46 | (2006.01) |
| A61B 6/00 | (2006.01) |
| G06T 7/00 | (2006.01) |
| A61B 6/03 | (2006.01) |

(52) U.S. Cl.
CPC ............ *G06K 9/4642* (2013.01); *A61B 6/5217* (2013.01); *G06T 7/0016* (2013.01); *A61B 6/037* (2013.01); *G06T 2207/10081* (2013.01); *G06T 2207/10104* (2013.01); *G06T 2207/20104* (2013.01); *G06T 2207/30096* (2013.01)
USPC ........................................................ 382/128

(58) Field of Classification Search
USPC ........................................................ 382/128
See application file for complete search history.

(56) References Cited

U.S. PATENT DOCUMENTS

| | | | | |
|---|---|---|---|---|
| 5,179,581 A | * | 1/1993 | Annis .............................. | 378/57 |
| 5,579,402 A | * | 11/1996 | Hayen ........................... | 382/132 |
| 6,567,684 B1 | * | 5/2003 | Chenevert et al. ............. | 600/410 |
| 6,909,794 B2 | * | 6/2005 | Caspi ............................. | 382/128 |
| 7,327,865 B2 | * | 2/2008 | Fu et al. ......................... | 382/128 |
| 7,499,578 B2 | * | 3/2009 | Reeves et al. ................. | 382/128 |
| 2004/0064038 A1 | | 4/2004 | Bruder et al. | |
| 2004/0260176 A1 | | 12/2004 | Wollenweber et al. | |
| 2005/0238253 A1 | * | 10/2005 | Behrenbruch et al. ........ | 382/294 |
| 2006/0066469 A1 | * | 3/2006 | Foote et al. ..................... | 342/22 |
| 2007/0100226 A1 | | 5/2007 | Yankelevitz | |
| 2008/0080614 A1 | * | 4/2008 | Munoz et al. ............ | 375/240.01 |
| 2008/0080770 A1 | | 4/2008 | Mendonca | |
| 2008/0095417 A1 | * | 4/2008 | Pedrizzetti et al. ........... | 382/128 |
| 2008/0118134 A1 | | 5/2008 | Sirohey | |
| 2008/0232669 A1 | * | 9/2008 | Piper et al. ..................... | 382/133 |

(Continued)

FOREIGN PATENT DOCUMENTS

| | | |
|---|---|---|
| WO | 2005077263 A2 | 8/2005 |
| WO | 2007/026234 A1 | 3/2007 |

OTHER PUBLICATIONS

Medical Imaging Matching—A Review With Classification, van den Elsen, Pol, and Viergever, IEEE Engineering in Medicine and Biology, vol. 12, No. 1, pp. 26-39, 1993.*

(Continued)

*Primary Examiner* — Christ Mahoney
(74) *Attorney, Agent, or Firm* — Thomas | Horstemeyer, LLP.

(57) ABSTRACT

Systems, methods and computer program products identify first biologic data in a region of interest in a first image and calculate a first biologic volume histogram from the first biologic data. Second biologic data in the same region of interest is identified in a second image and a second biologic volume histogram is calculated from the second biologic data. A difference in intensity for the region of interest is determined using the first biologic volume histogram and the second biologic volume histogram.

30 Claims, 11 Drawing Sheets

(56) References Cited

U.S. PATENT DOCUMENTS

2008/0310697 A1* 12/2008 Razifar et al. ............... 382/131
2009/0279758 A1* 11/2009 Dikici et al. ................. 382/128

OTHER PUBLICATIONS

Fox et al., Poster presentation titled "Metabolic Volume Histograms and Voxel Map Response: SUV-Based Treatment Response Assessment Methods Using PET-CT". Poster displayed at American Radium Society in Los Angeles, CA. May 2008.

Fox et al., "Metabolic Volume Histograms and Voxel Map Response: SUV-Based Treatment Response Assessment Methods Using PET-CT". *Oncology*. 22(4S1): 49. 2008 (abstract).

Marks et al., "The Role of Three Dimensional Functional Lung Imaging in Radiation Treatment Planning: The Functional Dose—Volume Histogram". *Int. J. Radiation Oncology Biol. Phys*. vol. 33, No. 1, pp. 65-75. 1995.

International Search Report and the Written Opinion of the International Searching Authority, or the Declaration, Application No. PCT/US2009/045640, Jan. 27, 2010, 11 pages.

Patent Examination Report for co-pending AU Patent Application No. 2009260422.

Office Action for related Canadian application No. 2,726,539 dated May 1, 2014.

Office Action form co-pending CA Application No. 2,726,539, mailed May 1, 2014.

* cited by examiner

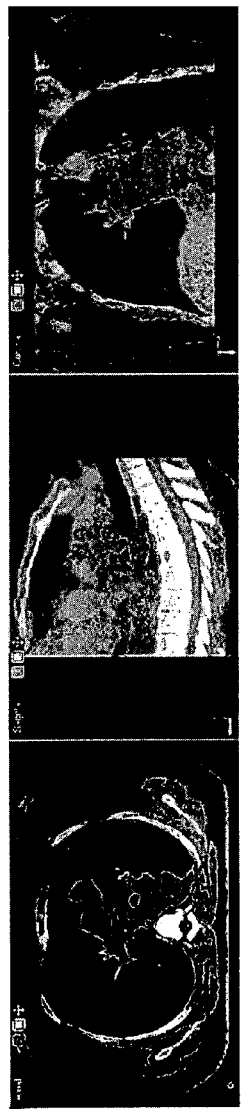
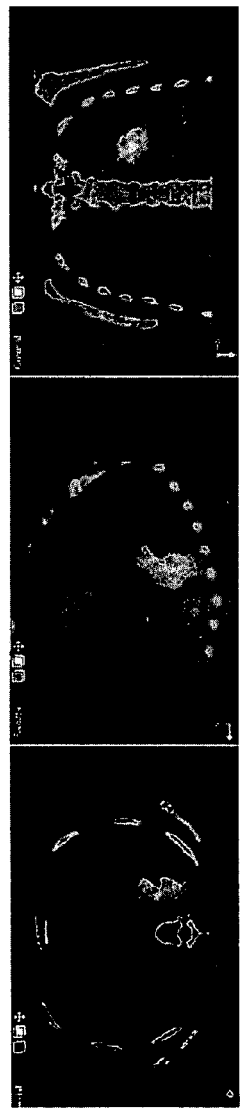
FIG. 11A
FIG. 11B
FIG. 11C

ASSESSING TUMOR RESPONSE TO THERAPY

FIELD

This document relates to a metabolic volume analysis method for assessing response of a tumor to therapy.

BACKGROUND

Fluorodeoxyglucose (FDG) positron emission tomography (PET) imaging is useful in the detection of lymph node metastases including, for instance, lung cancer, head and neck tumors, and esophageal cancer. In particular, qualitative image interpretation of FDG PET images has been useful for tumor detection and staging. Further, FDG PET measurements have been applied to identify the response of malignant tumors to therapy.

SUMMARY

Disclosed herein are methods, systems, and computer program products for assessing tumor response to therapy. In an implementation, a method includes identifying first biologic data in a region of interest in a first image, calculating a first biologic volume histogram from the first biologic data, identifying second biologic data in the region of interest in a second image, calculating a second biologic volume histogram from the second biologic data, and determining a difference in intensity for the region of interest using the first biologic volume histogram and the second biologic volume histogram.

One or more of the following features may also be included. The intensity for the region of interest may be a metabolic intensity. The first biologic data can include first metabolic distribution data, and the second biologic data can include second metabolic distribution data. The first image and the second image and second image can also be registered, for instance, using rigid, elastic, and/or deformable image registration.

Calculating a first biologic volume histogram can include calculating a cumulative metabolic volume histogram. Additionally, calculating a first biologic volume histogram can include calculating a differential metabolic volume histogram. According to another feature, the method can include identifying a plurality of volume elements within the region of interest. The plurality of volume elements can include, for instance, voxels.

According to yet another feature, the method can include calculating a metabolic intensity value from the first image at each of the plurality of volume elements. Calculating the first metabolic volume histogram can be based at least in part on the calculated metabolic intensity values for each of the plurality of volume elements. Further, the first image can include a PET image.

According to yet another feature, the method can include identifying a plurality of sub-regions of interest within the region of interest. Identifying a plurality of sub-regions of interest can also include identifying the plurality of sub-regions of interest based on a center of mass of the region of interest. Additionally, identifying a plurality of sub-regions of interest can include identifying the plurality of sub-regions of interest by parsing the region of interest into sections separated by radial spokes sharing the center of mass as a termination point.

Furthermore, identifying first metabolic data in the region of interest in a first image can include identifying metabolic activity data from the first image in at least one of the plurality of sub-regions of interest. Similarly, identifying second metabolic data in the region of interest in a second image can include identifying metabolic activity data from the second image in the at least one of the plurality of sub-regions.

According to another feature, the method can include comparing the first metabolic activity data and the second metabolic activity data. According to yet another feature, the first metabolic activity data and the second metabolic activity data can include a metabolic volume histogram, a maximum SUV, or a minimum SUV. According to yet another feature, the method can include identifying at least one location in the region of interest where the first metabolic activity data differs from the second metabolic activity data.

These general and specific aspects may be implemented using a system, a method, or a computer program, or any combination of systems, methods, and computer programs.

BRIEF DESCRIPTION OF THE DRAWINGS

Reference will now be made to the accompanying drawings, which are not necessarily drawn to scale, and wherein:

FIGS. 11A-C is an example image registration accuracy comparison.

DETAILED DESCRIPTION

Figure 1:
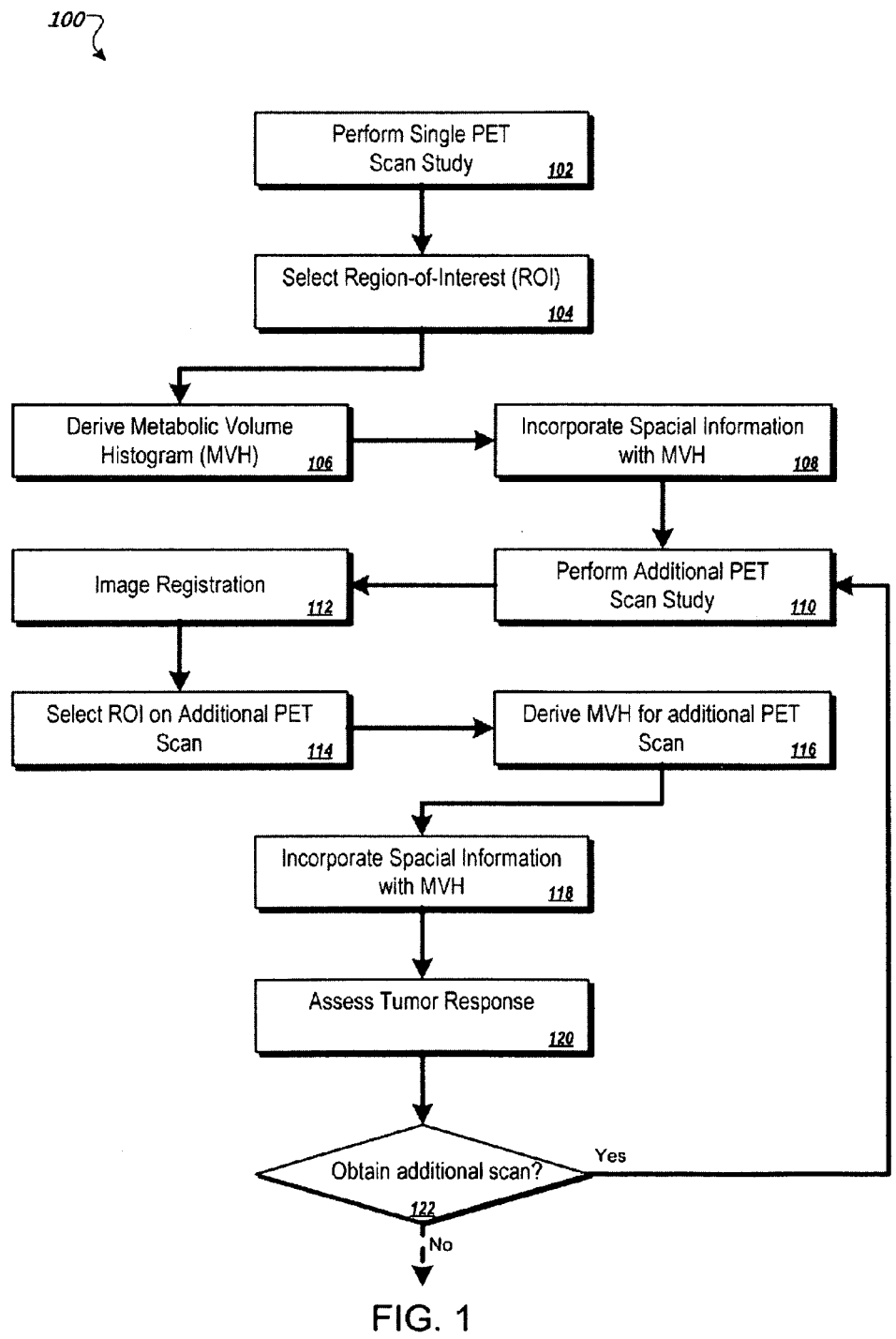
FIG. 1 is a flow diagram of an example process of quantitatively assessing tumor response.

Referring to FIG. 1, a process 100 can be utilized to quantitatively assess a tumor volume response for a patient over a period of time based, at least in part, on data obtained from Fluorodeoxyglucose (FDG) positron emission tomography (PET) and/or Computerized Tomography (CT) scans. The process 100 can include a number of operations that are performed by an imaging system capable of performing PET scans and/or a computational system, such as a personal computing workstation. In operation 102 of the process 100, a single PET scan study can be performed. A single study can be one or more PET scans performed within a period of time (e.g., 45 minutes) that are merged into a single result. The PET scan studies can produce three-dimensional images of functional processes in the body by detecting positron emissions of radioactive tracer isotopes that are incorporated into compounds readily used by the body (e.g., glucose, water, ammonia, and the like) and injected into a subject. Currently, the most commonly used molecule is fluorodeoxyglucose, where the radioactive isotope is fluorine-18. Simultaneous to the PET scans, CT scans can be performed to provide detailed pictures of the internal anatomy that can reveal the location, size, and shape of anatomical features (e.g., bones, organs, and the like) and abnormal cancerous growths.

The result of a PET and simultaneous CT scan can be a three-dimensional map of the detected area (e.g., the head) indicating levels of metabolic and functional (collectively, biologic) activity along with corresponding anatomical structures. While the data obtained from the PET scan can be numeric (e.g., metabolic intensity values), it is often displayed graphically with colors representing areas of differing metabolic activities (e.g., metabolic hot and cold spots based on metabolic activity values). When used in tumor diagnosis, metabolic hot spots can be identified and used to select one or more regions of interest that potentially contain malignant tumors. In some examples, PET scans can be performed at multiple periods in time (e.g., before a therapy, after a therapy, half-way through a therapy, and the like) to assess the changes in a region of interest over time (e.g., in response to a prescribed therapy).

In some embodiments, such as the one described in connection with FIG. 1, PET scans (which show metabolic activity) can be performed simultaneously with CT scans (which show anatomic structures) for the purpose of identifying and locating the metabolic data obtained using the PET scan with respect to anatomical structures (e.g., bones, organs, etc). In alternative embodiments, PET scans can be performed simultaneously with other types of structural scans (e.g., MRI scans, or the like). When performing PET scans simultaneously with structural scans (such as CT scans), the scans can be fused (i.e., co-registered) into a single image with a single coordinate system. When co-registered, the new image will contain both biologic (e.g., metabolic) activity and anatomical structures. In this way, areas of high biologic (e.g., metabolic) activity (e.g., potential malignant tumors) can be identified and described relative to anatomical structures (such as bones, lungs, or the like). In still other embodiments, the PET scans can be performed without performing any type of structural scans. When performing processes, such as the process 100, that utilize a PET scan study, a PET scan can be used alone or can be fused with other types of scans which identify anatomical data (e.g., MRI scans, or the like) without negatively affecting the results obtained with the process.

Still referring to FIG. 1, in operation 104 a region-of-interest (ROI) that includes, for example, a malignant tumor is selected. Once an ROI is identified, it can be divided into one or more sub-regions or volume elements (described in more detail below, in connection with FIGS. 4-5), each with a corresponding metabolic activity derived from the PET scan data.

As described previously, the result of a PET scan can include biologic (e.g., metabolic) intensity values for regions of the body included in the scan. In some embodiments, the intensity values can be reported, and subsequently used for further analysis, by organizing them into a histogram, such a biologic value histogram (BVH). Although the present specification describes a biologic volume histogram, which can include metabolic activity and functional activity, the remainder of the specification is described only with respect to a metabolic volume histogram for illustrative purposes, which is one type of biologic value histogram.

Figure 6:
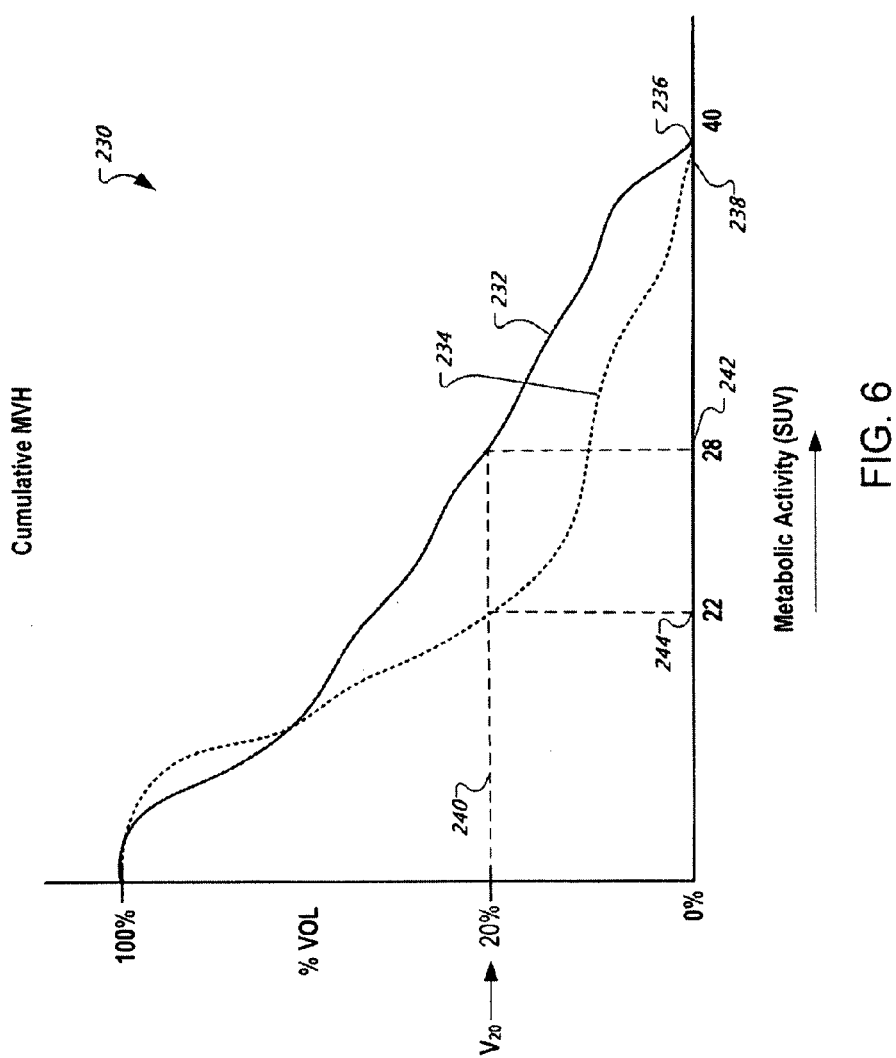
FIG. 6 depicts an example metabolic value histogram.

Operation 106 can include deriving an MVH which summarizes metabolic distribution information for a region of interest. The MVH can be used to identify characteristics such as metabolic uniformity, functional uniformity, and metabolic hot and cold spots. An exemplary MVH, derived for the selected region of interest, can show, for example, the number of sub-regions associated with a particular metabolic intensity or the total volume associated with a particular metabolic intensity. Another exemplary type of MVH, the cumulative MVH (examples of which are shown in FIG. 6), plots the volume with metabolic intensity value that is greater than or equal to a given metabolic value against the given value over the entire range of measured metabolic intensity values.

While an MVH can provide details about the mathematical distribution of metabolic intensities, introduction of spatial information can be used to show geometric information about measured metabolic intensities. In some implementations, spatial information can be added to the MVH to provide additional criteria for tumor assessment (described in more detail in connection with FIGS. 7-8). For example, in operation 108, quantitative spatial information (e.g., how the metabolic intensities are spatially distributed) is incorporated with the MVH from operation 106.

In operation 110, an additional PET scan study can be performed at a different point in time (e.g., after therapeutic treatment such as chemotherapy) to obtain an additional set of data containing the same ROI (or a greater region inclusive of the ROI) selected in operation 104. When more than one scan is available (e.g., two or more PET scans), it is advantageous, for example when comparing tumor location, to transform the results of all scans to a single coordinate system. In optional operation 112, image registration techniques (e.g., static registration, elastic or deformable registration, and the like) can employed to transform the two data sets to a single coordinate system. Once two or more scans are transformed to a single coordinate system, the identical region-of-interest (ROI) can be identified on all scans. While choosing the identical ROI on multiple scans is beneficial, it should be understood that slightly different ROIs can be identified and used in subsequent steps without negatively affecting the process 100. In operation 114, an ROI on the PET scan study from operation 110 is selected based, at least in part, on the ROI from the PET scan study obtained in operation 102. In operation 116, an MVH for the ROI selected in operation 114 is derived. In operation 118, quantitative spatial information is incorporated with the MVH from operation 116.

Once data is determined and/or derived from multiple PET scans (e.g., metabolic intensity values), the data from one scan can be compared to the data from one or more additional scans (e.g., for determining the response of a tumor to a prescribed therapy). For example, if a subsequent scan yields a MVH that shows lower metabolic intensities than the previous scan, it may be determined that a tumor is responding positively to a therapy. In operation 120 the tumor response is assessed by examining the MVH derived during operation 116 and the spatial information incorporated during operation 118 and comparing this information to the MVH and spatial information determined in operations 116 and 118. As additional scans are performed, more comparisons can be made showing tumor response. Operation 122 can cause the process 100 to return to operation 110 and operations 110 through 118 can be repeated to obtain additional PET scan studies and perform further comparisons to the initial scan.

Operations 110 through 118 can be completed as many times as required, each time producing an additional PET scan and subsequent comparison to the initial scan. While this implementation describes comparing subsequent scans to the original scan, all scans in a study can be compared. For example, if five scans are performed (e.g., numbered "1" through "5"), the results of scans "2" through "5" could be compared to the results of scan "1". In addition, or in the alternative, the results of scans "5" and "1" through "3" could be compared to the results of scan "4". Also, the results of scan "5" could be compared to the results of scan "2", the results of scan "3" could be compared to the results of scan "4", and the like. While FIG. 1 depicts a specific sequence of events for the process 100, it should be clear to someone skilled in the art that these steps need not necessarily be performed in the particular order described.

In an alternate implementation, a plurality of PET scan studies (e.g., operations 102 and 110) could all be performed before any additional analysis (e.g., operations 104-108) are performed. Analysis of one PET scan study need not necessarily be performed prior to performing an additional study. In further implementations, the baseline data (e.g., ROI, MVH, quantitative spatial information, and the like) need not be derived from the first PET scan study performed. For example, the ROI could be selected from the second scan and used, at least in part, to select the ROI in all other PET scan studies.

In some implementations, as in the one described above in association with FIG. 1, a region of interest (ROI) can be chosen from a PET scan. The ROI can be chosen to include a tumor whose response to a therapy is to be assessed. As described previously, a first set of metabolic data from a region of interest (ROI) in a first image can be used to derive a metabolic volume histogram (MVH). In order to create an MVH from a chosen ROI, the ROI can be divided into smaller sub-units, or voxels, each of which can have a volume, a volumetric center, and a metabolic rate associated with it. With this data, information about the ROI, such as total volume, can be determined. In addition, statistical analysis of the voxels can be performed to determine information, such as the mathematical distribution of metabolic intensities within the ROI. For example, an ROI can be divided into a plurality of equally sized volume elements, or voxels, in which the metabolic data of these voxels can be used in the calculation of a metabolic value histogram (described below).

Figure 2:
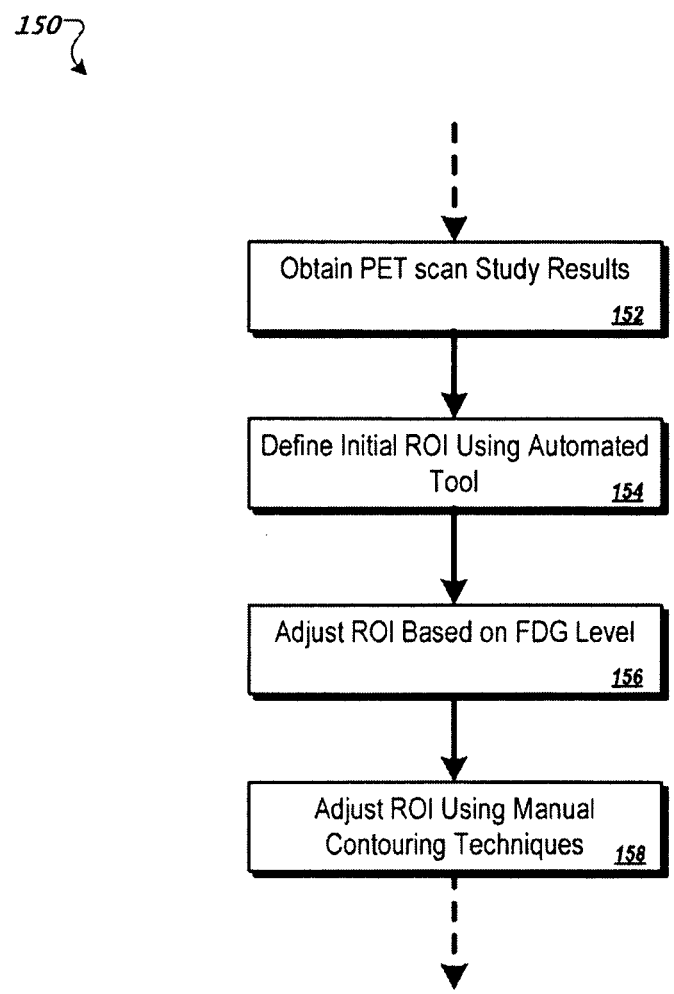
FIG. 2 is a flow diagram of an example process of selecting a region of interest.

Referring to FIG. 2, a process 150 can be utilized to select a region of interest (ROI) from data acquired during a PET scan. The process 150 may include a number of operations that are performed by an imaging system capable of performing PET scans and/or a computational system, such as a personal computing workstation. In operation 152, a PET scan study result (e.g., from a PET scan study such as performed by operation 102) is obtained and can be transferred to a computer workstation. An initial region of interest (ROI) can be selected by a diagnostic image processor, such as "Pro Assist" using techniques that are familiar to someone skilled in the art. For example, in operation 154, iso-lines (e.g., iso-intensity lines, iso-SUV lines, and the like) can be identified, displayed and utilized, at least in part, to automatically identify an initial ROI. In operation 156, the initial ROI can be refined. In some embodiments, the initial ROI can be refined, at least in part, by selecting one or more continuous regions that correspond to values that are all greater than a comparative value. For example, a continuous region can be identified where the fluorodeoxyglucose (FDG) levels within the chosen region are all greater than a pre-determined percentage (e.g., 50%) of the maximum fluorodeoxyglucose (FDG) level within the initially determined region. In operation 158, a user may employ manual contouring methods to modify the previously determined region utilizing a graphical user interface, such as a computer workstation. The determined ROI can later be used to derive a metabolic value histogram (MVH), such as that derived by operation 106 in FIG. 1, for the purpose of quantitatively assessing a tumor. Creation of an MVH will be discussed in greater detail in connection to FIG. 4. While the previously described process 150 depicts a specific sequence of events, an ROI can be selected using any one or more of the events listed previously (in any order), or by other means not described here.

Figure 3A:
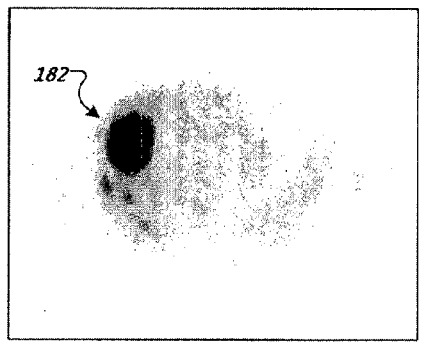
FIGS. 3A-C depict portions of a PET scan, a CT scan, and a CT/PET fusion, respectively.
Figure 3B:
Figure 3C:
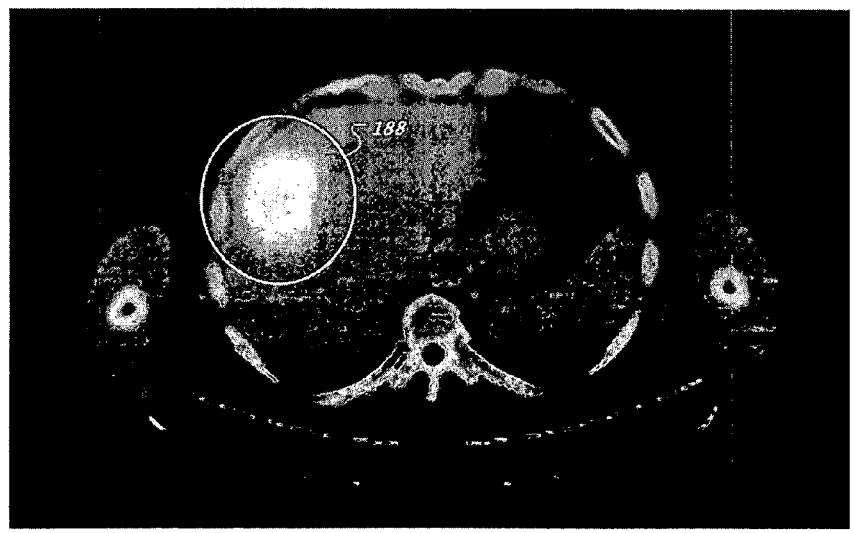

Referring to FIG. 3A-C, a process used to identify an ROI (e.g., the process 150) can be used identify an ROI associated with, for instance, a lung tumor. FIG. 3A depicts a transverse slice 180 of a PET scan image with a region of high uptake 182 (shown as a dark region in FIG. 3A). In some implementations, a simultaneous CT scan (a transverse slice 184 of which is depicted in FIG. 3B) can be performed for identifying anatomical structure. In some implementations, the CT and PET scans can be combined into a single coordinate system (i.e., co-registered), yielding a combined CT/PET scan, a transverse slice 186 of which is depicted in FIG. 3C. The resulting CT/PET image can be used to identify a region of interest (ROI) 188. The identification of the ROI 188 can be done in an automated manner, manually, or a combination of both, an example of which was described previously with regard to FIG. 2. In some implementations, after an ROI 188 is selected in an automated manner, a user may manually modify the ROI 188 using manual contouring methods known to one skilled in the art (e.g., using a computer workstation mouse to draw or modify the ROI 188 on the PET scan image). While the implementations here describe a specific series of events for determining the ROI 188, other methods for determining a region of interest can be employed without diverging from the spirit of the process 150.

Figure 4:
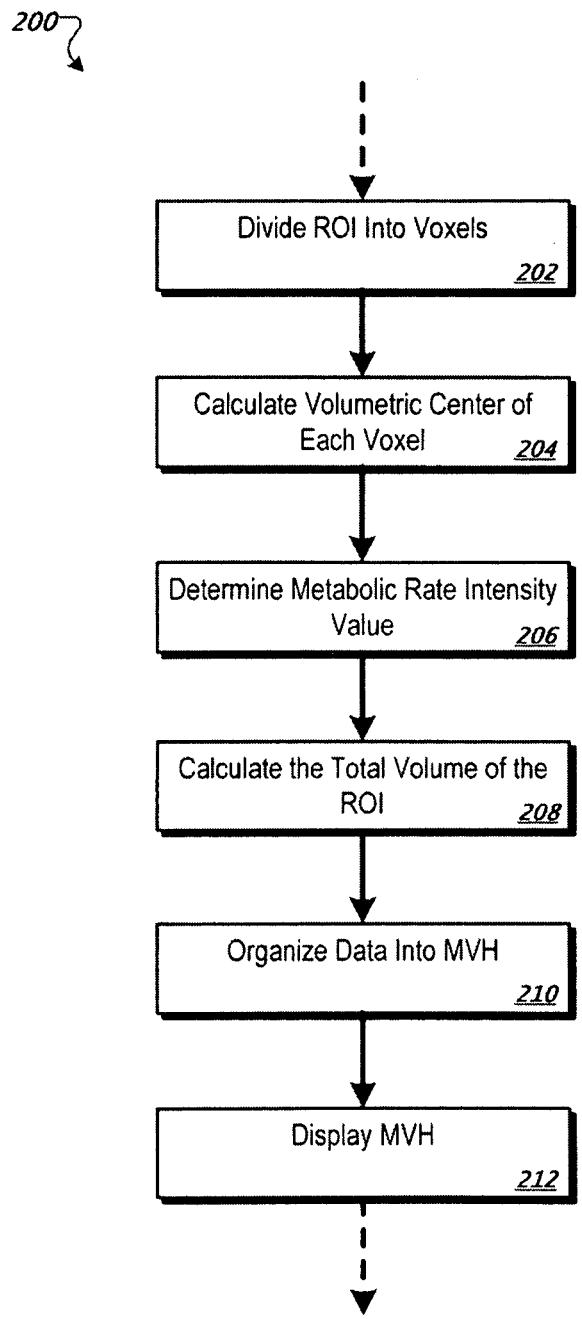
FIG. 4 is a flow diagram of an example process of creating a metabolic value histogram.

Referring to FIG. 4, a process 200 can be utilized to create a metabolic volume histogram (MVH) from data acquired during a PET scan. The process 200 may include a number of operations that are performed by an imaging system capable of performing PET scans and/or a computational system, such as a personal computing workstation. As described previously, an ROI can be divided into sub-regions. In some embodiments, these sub-regions are equally sized volumes (e.g., equally sized cubes referred to as voxels). For example, in operation 202, a previously determined ROI is divided into equally sized volumes (i.e., voxels). In some implementations, the process 200 can use the same voxel size, as was previously defined during the PET study from which the ROI was derived, to determine the voxel size in operation 202. Operation 204 is performed and calculates the volumetric center of each voxel. In operation 206 the metabolic rate intensity value for each voxel can be selected or calculated from the PET study data and associated with its corresponding volumetric center. For example, the metabolic rate intensity value can be based on standardized uptake values (SUV), which is a process for assessing the metabolic uptake of tumors across different patients and/or can be in absolute radioactive uptake such as Bq/cc.

Figure 5:
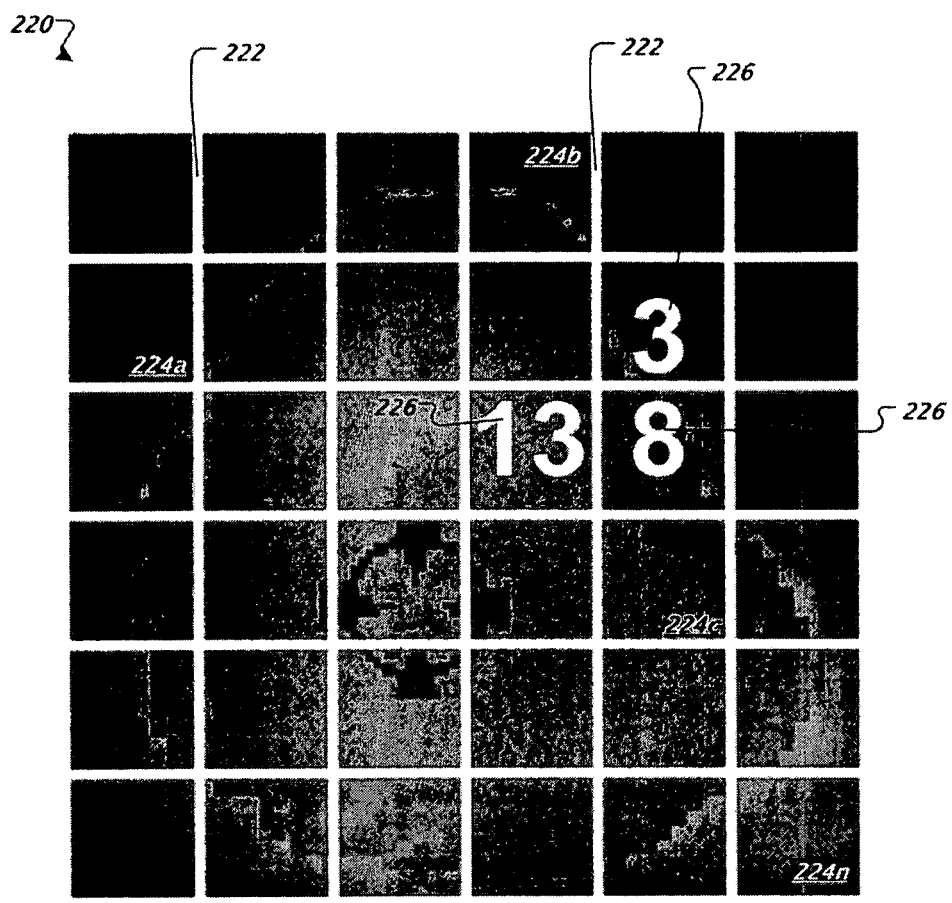
FIG. 5 depicts an illustrative slice of a region of interest divided into voxels.

FIG. 5 depicts an illustrative two-dimensional slice of a PET scan image corresponding to an ROI 220. In the implementation shown, the slice includes gridlines 222 showing two dimension slices of individual voxels 224. In the example of FIG. 5, the slice is divided into 24 voxels 224 (224a, 224b, 224c, and 224n are shown) by the gridlines 222. Some of the voxels 224 have their associated metabolic intensity values 226 displayed. The metabolic intensity values 226 can be calculated for each voxel, for example, by image processing that registers the intensity of the image at the center of each voxel. While FIG. 5 depicts a region of a single slice of a PET scan image, more than one slice may be required to show all voxels associated with an ROI.

Referring again to FIG. 4, in operation 208 the total volume of the ROI is calculated, for example, by summing the total number of voxels and multiplying the sum by the volume of each voxel. Operation 210 is performed and the data is organized into a metabolic volume histogram (MVH) (examples of which are shown in FIG. 6). In some implementations, an MVH can be similar to a mathematical histogram in that accumulated volume elements (e.g., voxels) with intensity values in specified metabolic intensity intervals are plotted against a set of equispaced metabolic intensity intervals. This type of MVH may be referred to as a differential MVH. An exemplary differential MVH can be derived by accumulating voxels into groupings of iso-intensity. For example, intensities can be rounded to the nearest integer (e.g., 13, 8, 5, and the like) and the total volume of the voxels with intensity values that correspond to each of the integer values can be added up. Subsequently, the total volume of all voxels associated with each integer value can be plotted against the corresponding integer value. In addition or in the alternative, a cumulative MVH can be derived by plotting the volume with a metabolic intensity value greater than or equal to a given metabolic value against that metabolic value over the entire metabolic intensity range. The volume data can be displayed as, for example, absolute volume or percent volume. In operation 212, the results (e.g., the differential MVH, the cumulative MVH, or the like) can be displayed.

Referring to FIG. 6, in some embodiments, an MVH derived from a PET scan can be used in conjunction with one or more MVHs from additional PET scans to, for example, diagnose a tumor, determine a therapy to treat a tumor, and/or assess the response of a tumor to a therapy. For example, two or more cumulative MVHs can be displayed on a single cumulative MVH graph 230 for the purpose of comparison. In this example, a pre radiation treatment (pre-Tx) curve 232 is displayed with a post-Tx curve 234. In some implementations, metabolic activity (e.g., SUV) is used to assess tumor response. In cases where SUV is used, multiple types of SUV can be used. In one case, the maximum SUV value identified in an ROI can be used. In the example depicted in FIG. 6, the maximum SUV 236 of the pre-Tx curve 232 is 38, while the maximum SUV 238 of the post-Tx curve 234 is 37, representing a one unit (or 3%) decrease. In some implementations, the mean SUV can be used to assess tumor response. In the case of the curves 232 and 234, the mean value of each curve is 15, representing no change. In some implementations, the SUV associated with a predetermined percentage of the ROI volume can also be used. For example, the SUV value associated with 20% of the ROI volume, also called the $V_{20}$, can be used to assess tumor response. In FIG. 6, the $V_{20}$ line 240 is used to determine the $V_{20}$ SUV 242 of the pre-Tx curve 232, which is 28 and the $V_{20}$ SUV 244 of the post-Tx curve 234, which is 22. Using the $V_{20}$ SUV indicates an approximate 20% decrease in metabolic activity of the ROI between the pre-Tx scan and the post-Tx scan.

Figure 7:
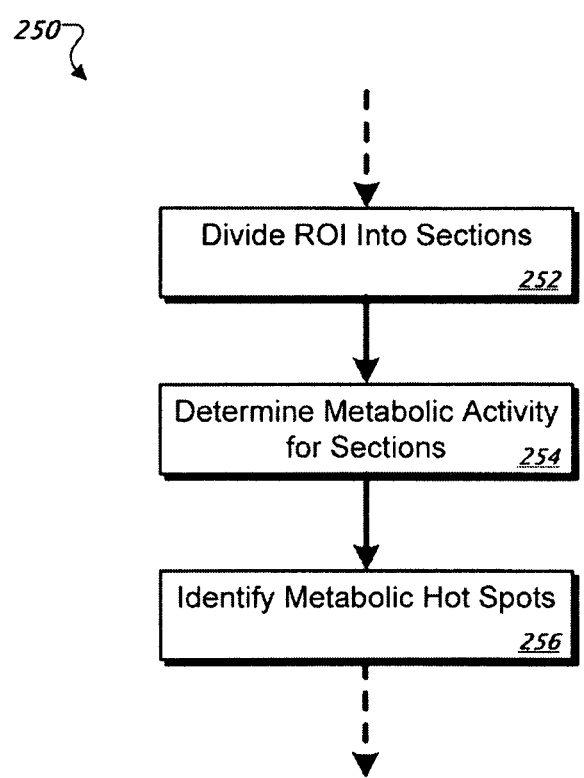
FIG. 7 is a flow diagram of an example process for incorporating spatial information into an MVH.
Figure 8:
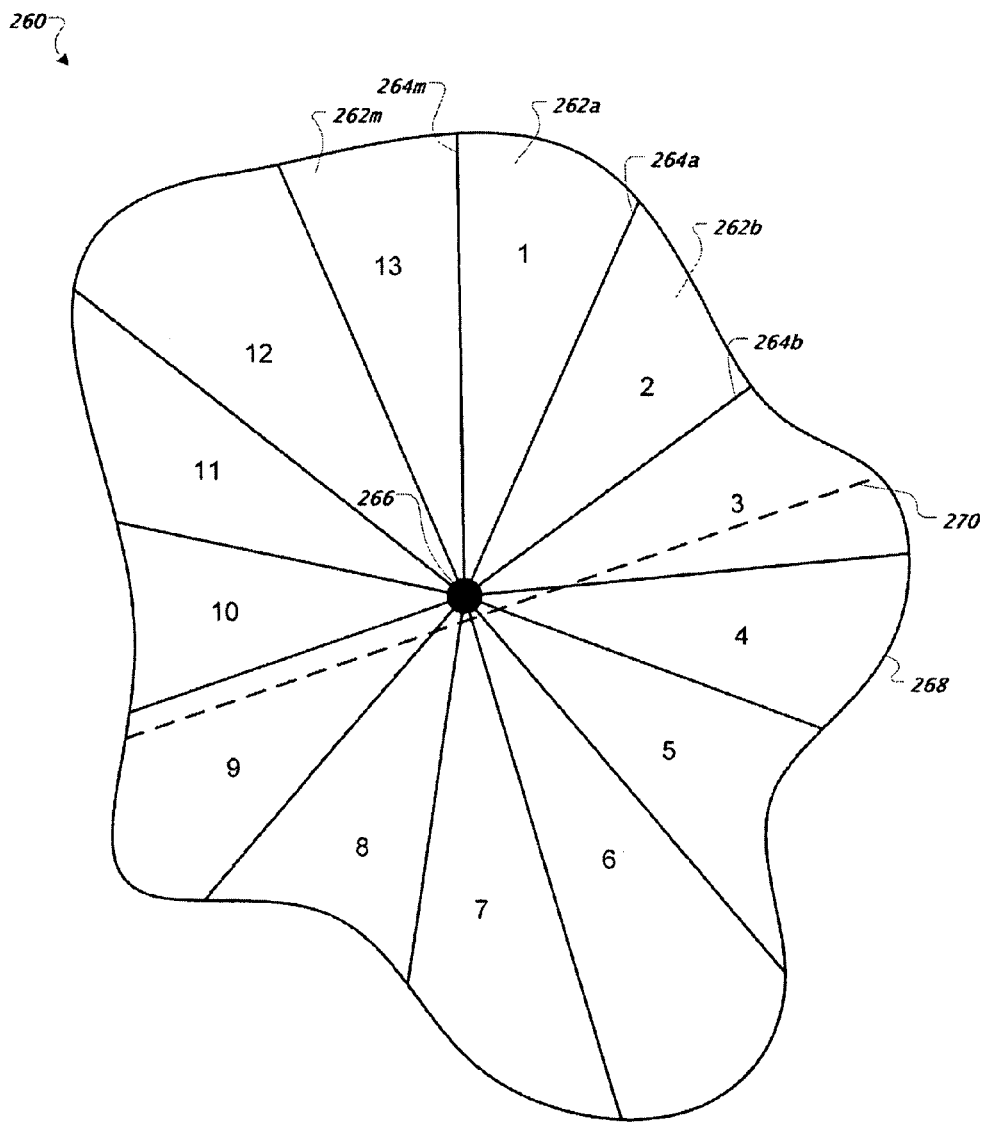
FIG. 8 is an example region of interest divided into sections.

Referring to FIG. 7-8, in addition or in the alternative to using an MVH, spatial information can be used to aid in the diagnosis of a tumor, the determination of therapy to treat a tumor, and in assessing the response of a tumor to an implemented therapy. For example, a process 250 (FIG. 7) can be utilized to incorporate quantitative spatial information about an ROI 260 (FIG. 8) with an MVH. The process 250 may include a number of operations that are performed by an imaging system capable of performing PET scans and/or a computational system, such as a personal computing workstation. In operation 252, the previously determined ROI 260 is divided into sections (or 'sub-regions' of interest). As shown in FIG. 8, an illustrative ROI can be divided into a predetermined number of pie shaped sections (or 'sub-regions'). For example, an ROI 260 in FIG. 8 can be divided in thirteen sections 262 (262a, 262b, and 262m are shown) using radial spokes 264 (264a, 264b, and 264m are shown) that emanate from a center of mass 266 and travel outward until intersecting a boundary 268. In operation 254, the metabolic activity for each section 262 is determined. In the embodiment described in connection with FIG. 7, the metabolic activity for each section 262 can be the SUV (determined from the PET scan data) for that section 262. In other implementations, the metabolic activity may be an absolute radioactivity uptake and reported in units such as Bq/cc. The metabolic activity for a section can be, for example, the maximum, minimum, or mean intensity value recorded in that section.

In operation 256, the sections 262 can be used to represent and quantitatively assess the spatial locations of hot spots (i.e., areas of high metabolic activity) and cold spots (i.e., areas of low metabolic activity). After registration to another scan (described later in connection with FIG. 9A-D) this representation can be used to assess changes in the geometric shape, dimension, and relative location of a tumor and/or ROI. In some embodiments, a maximum length or longest dimension 270 (FIG. 8) can be identified on the ROI 260 which represents the longest straight line that can be drawn from one point on the boundary 268 to another point on the boundary 268. This longest dimension 270 can be compared to the longest dimension of another ROI (not shown) for the purpose of assessing tumor growth or contraction. This comparison can be reported, for example, as an actual change in size, or as a percentage change in size. In some implementations, one or more methods (e.g., shape subtraction method) can be used to assess the difference between tumor volumes on multiple PET images acquired at different times. The results of the process can be areas of increased, decreased, or static metabolic activity and can be used to assess tumor response.

Figure 9B:
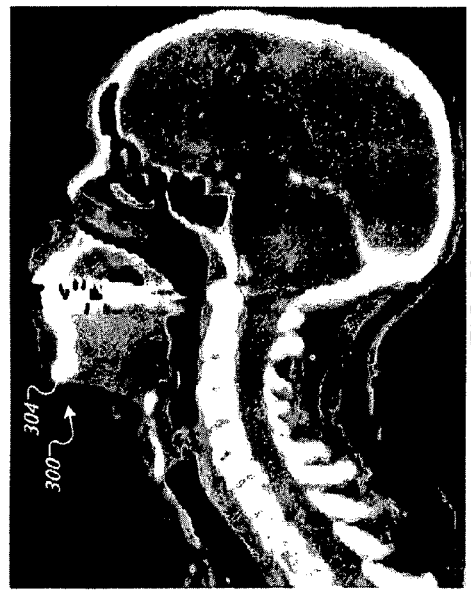
FIGS. 9A-D show example images before and after image registration.
Figure 9D:
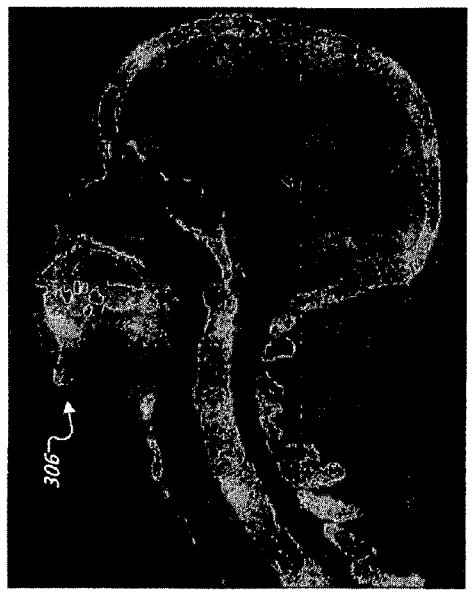
Figure 9A:
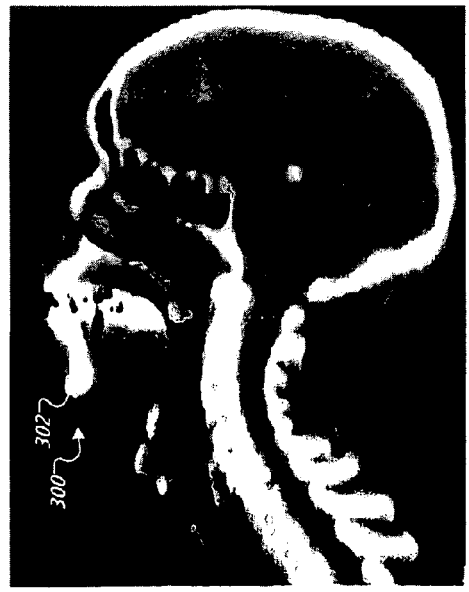

Referring now to FIGS. 9A-D, one or more PET scans from different points in time (e.g., before beginning a therapy, during the course of a therapy, after completion of a therapy, or the like) can be registered for the purpose of comparing them. As would be understood by someone skilled in the art, when PET scan are taken at different points in time, the result is two different data sets and/or images that are not oriented in the same coordinate axes. When subsequent scans are performed, the health care practitioners administering the scans attempt to place a patient in exactly the same location as he/she was in for prior scans. While this ensures that subsequent data sets are relatively close, computation methods, such as image registration, can be used to transform the different data sets into a single coordinate system, thereby making it easier to compare the two data sets. In some embodiments, data from a simultaneous CT scan (e.g., the anatomical data from the scans) can be co-registered with the PET scan data to derive a set of PET/CT scan data. The CT portion of the scan data can be used to register the PET/CT scan data to one or more subsequent sets of PET/CT scan data. When registered, the two or more sets of PET/CT scan data can contain both metabolic activity and anatomical structures that are all organized in the same coordinate system. In this way, areas of high metabolic activity (e.g., potential malignant tumors) can be compared from one PET/CT scan to another to determine the progression or regression of a tumor after a period of time Referring now to FIGS. 9A-B, FIG. 9A is a single slice of a representation of data acquired from an individual using a CT scan. FIG. 9B is slice of a representation of data from a subsequent CT scan acquired from the same individual at a later point in time. In this example, the two images can be registered using rigid registration techniques to yield FIG. 9C. In rigid registration, the images are altered only by using translation (in three dimensions), rotation (around three axes of rotation), and scaling. As the patient was placed in the same position during both scans, the anatomical features of the two images register almost exactly. One area 300 that does not register as well is in the location around the chin. In this example, the patient may have had his/her mouth open slightly more in the scan represented by FIG. 9A than in the scan represented by FIG. 9B leading to chin 302 (FIGS. 9A and 9C) being visibly separate from chin 304 (FIGS. 9B and 9C) in the combined FIG. 9C.

In some embodiments, after two scans have been registered using static registration techniques, further optimization of the registration can take place by using elastic or deformable registration techniques. Deformable registration can include transformations that allow local warping of image features, thus providing support for local deformations, instead of only global transformations as with rigid registration. Deformable registration approaches include, for example, polynomial wrapping, interpolation of smooth basis functions (thin-plate splines and wavelets), and physical continuum models (viscous fluid models and large deformation diffeomorphisms). With standard static registration techniques (described previously), only seven variables need be included in the optimization (i.e., three axes of translation, three axes of rotation, and scaling), whereas deformable registration techniques can use thousands of variables in the optimization process. For this reason, optimization techniques can be utilized with the registration approach to lessen the computational workload associated with deformable registration.

Figure 9C:
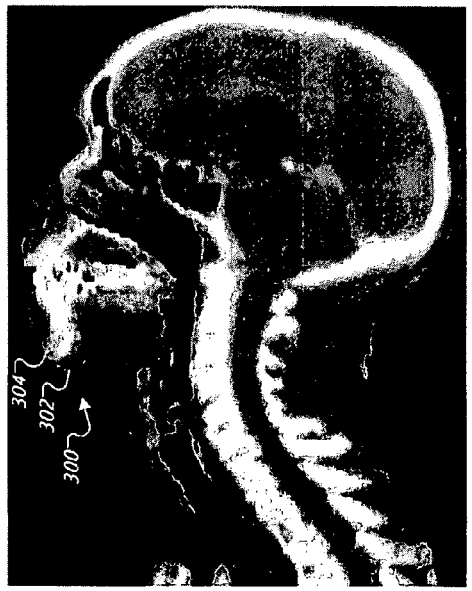

Referring now to FIG. 9D, in some implementations a B-Spline model can be used with a Mattes implementation of the mutual information metric and the bounded version of the limited memory Broyden-Fletcher-Goldfarb-Shanno algorithm (L-BFGSB) to perform a deformable registration of the data sets represented by FIGS. 9A-B, after rigidly registering them as shown in FIG. 9C. The resulting data sets are registered more accurately than is possible using rigid deformation techniques, as can be seen in an area 306 (FIG. 9D) in the area of the patient's chin. Additionally, the resulting registration can be color coded to show the amount of deformation employed during the deformable registration operation.

Figure 10:
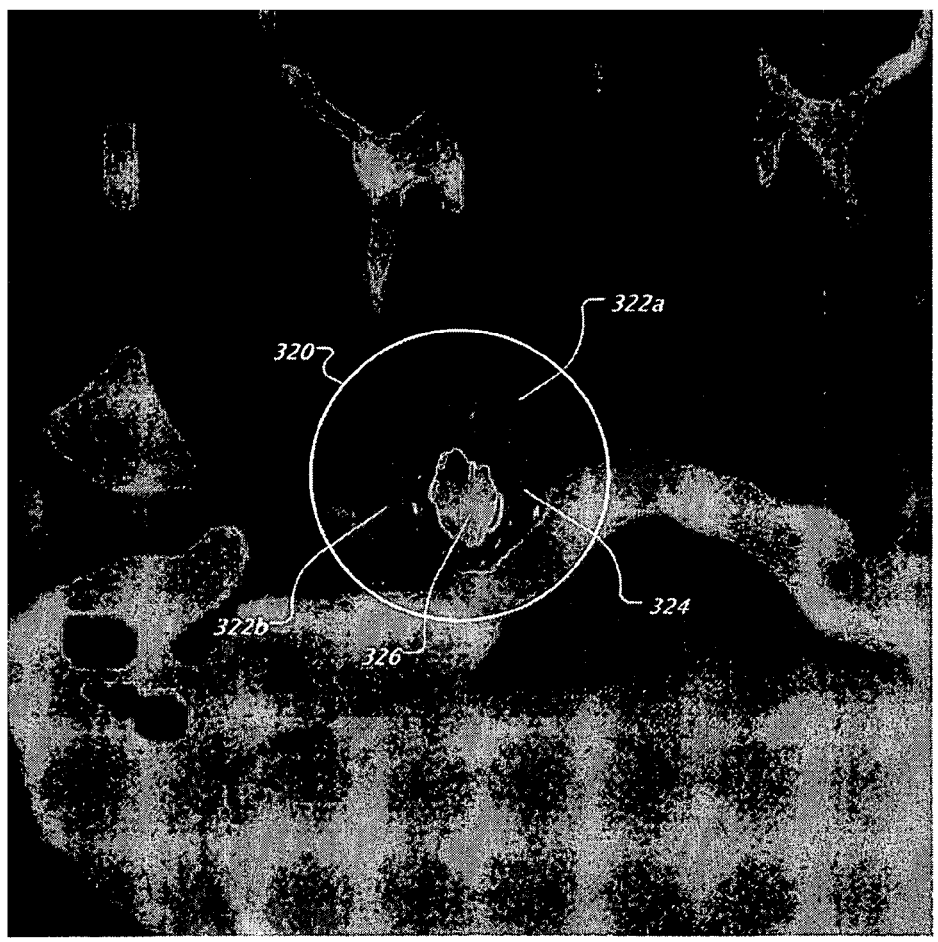
FIG. 10 is an example image having color-coded regions.

As described previously, the result of a PET scan can be co-registered to the results of a simultaneous CT scan to produce a three-dimensional map of a detected area indicating levels of metabolic activity (e.g., by color coding) along with corresponding anatomical structures. When used in identifying the progression (or regression) of a tumor, metabolic hot spots within a region of interest (ROI) can be compared from one PET scan to one or more subsequent PET scans (e.g., after administration of a therapy). As previously described, cumulative MVHs (FIG. 6) and spatial representations (FIG. 8) can be used to assess tumor progression. Additional, graphical, techniques can also be used to aid a medical practitioner in measuring tumor progression. For example, changes in a tumor can be displayed by color coding voxels in a region of interest (ROI). Referring now to FIG. 10, an ROI 320 is shown where the individual voxels are color code based on their progression from one scan to another. For example, voxels that show a decrease in activity, such as a lower standard uptake value, can be color coded in green, as with voxel regions 322a and 322b. Neutral regions can be coded blue, as with voxel region 324. Areas that show in increase in activity can be coded red, as with voxel region 326. This can allow a health care practitioner to visually differentiate one or more regions of a tumor that are increasing in metabolic activity from one or more areas that are remaining static, or decreasing in activity.

In some implementations, MVHs and/or spatial data derived from multiple PET scan studies (e.g., using the process 200) can be used to assess tumor response. For example, the following set of logical tests can be used to assess tumor response between one or more PET scan studies when the MVH has been calculated using SUV. In the example listed below, the change in SUV is used as one criterion for assessing tumor response. In this case the SUV used can be, for example, the maximum, minimum, or $V_{20}$ SUV value recorded on an MVH. A patient can be labeled as having a complete metabolic response, indicating complete remission, if the tumor is no longer identifiable on the later PET scan study.

A patient can be labeled as having progressive metabolic disease (PMD), indicating that tumor growth progressed, if at least one of three criteria (or logical tests) are satisfied. First, if there is a 25% or greater increase in metabolic activity as measured by SUV. Second, if there is a 20% or greater increase in the longest dimension of the tumor. Third, if there are new areas of FDG uptake.

A patient can be labeled as having a partial metabolic response (PMR), indicating a decrease in the tumor, if the following logical test is passed. If there is a decrease in SUV of greater than or equal to 15% after one cycle of treatment (e.g., chemotherapy) and a 25% or greater decrease after more than one treatment cycle.

A patient that does not pass the other logical tests are labeled as having stable metabolic disease (SMD), indicating that tumor growth was stable. In these cases, there is less than a 25% increase in SUV, less than a 15% decrease in SUV, a less than 20% increase in the longest dimension of the tumor, and no new areas of FDG uptake.

The above values for labeling a patient as having progressive metabolic disease, partial metabolic disease, and stable metabolic disease are illustrative only and different values or logical tests may be used. As an example, the first criteria for a patient labeled as having progressive metabolic disease may be satisfied by approximately a 15% or greater increase in metabolic activity, and the second criteria may be satisfied by approximately a 10% or greater increase in the longest dimension of the tumor.

In some embodiments, such as those described in connection FIG. 1, single sets of PET scan data can each be acquired at different points in time and compared to diagnose and assess the progression of tumors. Each set of PET scan data can be acquired during a scan, which can take 45 minutes or more to complete. This technique can be adequate for areas of the body that can remain still for the duration of a scan, such as the brain. However, for other areas of the body, such as the heart and lungs, a large number of cyclical movements can take place during the same amount of time, causing blurring and/or distortions in the scan results. In alternative embodiments, methods (e.g., a 4D PET/CT scan) can be used to identify cyclical movements of the body (e.g., breathing) and compensate for these movements by recording the results of the scan not as a single result, but as a set of results. For example, to perform a scan of a tumor located near or in the lungs, a gated PET scan can be performed where the results of the scan are categorized based on what point in the inspiration cycle the results were obtained in. For example, ten groups can be used to categorize the results of a 4D PET/CT scan, where each of the ten groups represents 10% of the breathing cycle, based on displacement of the users chest. At the end of the scan, the result can be ten separate sets of scan results, each representing 10% of the breathing cycle. The ten separate scan results can then be registered using deformable registration techniques (previously described in connection with FIGS. 9A-D) to produce a single scan result that has, at least in part, compensated for the movements of the patient associated with breathing.

In one exemplary embodiment, a patient with a primary pancreatic tumor was selected for 4D registration. The patient received 15 mCi 18FDG one hour prior to the PET image scan. A Real-time Position Management (RPM) system was employed by affixing a reflective block (used by the RPM system to determine what phase of the breathing cycle a patient is in) just below the xiphoid process. The patient was instructed to breathe regularly for the duration of the scan. The RPM camera recorded the anterio-posterior motion of the reflective block, while the PET scanner accumulated data in the gated PET mode for 10 minutes, recording 30 sequential frames of 0.2 sec each. The raw data from all frames were grouped to form a retrospectively gated scan at ten points during the respiratory cycle as measured by their respiratory trace amplitude.

In this exemplary embodiment, the 4D registration was employed to recover the respiratory motion. A typical registration accuracy comparison is presented in FIGS. 11A-C. FIGS. 11A and 11B show two resulting 4D data sets, from two different points in the respiration cycle, before registration. The 4D deformable registration was used to recover these changes, creating a direct one-to one correspondence between the two datasets, as observed in FIG. 11C where the differences between the two sets are eradicated. Consequently, a tumor can be correctly positioned after the registration, and distortion related to breathing can be minimized. Although not shown here, the registration was worked globally on all phases of the 4D PET-CT at once, creating a relatively motion-free dataset.

The methods and process flow diagrams described in this patent document may be implemented in computer processing systems including program code comprising program instructions that are executable by the computer processing system. For instance, the calculations for determining a MVH may be performed by computer program instructions. Other implementations may also be used. Additionally, the flow diagrams described in this document, which describe particular processes, may also be utilized to implement corresponding software structures and algorithms, and equivalents thereof.

Implementations described in this disclosure and all of the functional operations described in this specification can be implemented in whole or part with digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in an information carrier, e.g., in a machine-readable storage device or in a propagated signal, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code). A computer program can be deployed to be executed on one computer or on multiple computers at one site or distributed across multiple sites and interconnected by a communication network.

The processes described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

For instance, one or more graphical user interfaces (GUIs) may be used to display the images and/or results shown above. These GUIs may also be implemented by computer program instructions, including software, that may be manipulated by a user. One or more GUIs may also be manipulated by a user to alter and/or establish logical tests, including the values described above for identifying a patient as having progressive metabolic disease, partial metabolic disease, or stable metabolic disease.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

That which is claimed:

1. A computer system comprising:
   at least one processor; and
   memory, wherein said computer system is configured for:
      receiving a first image of a region of interest, said first image having been taken at a first time, and said region of interest being associated with a particular anatomical structure, where a boundary defines said region of interest in said first image;
      dividing said region of interest into a plurality of volumetric sub-regions of interest, said plurality of volumetric sub-regions of interest defined by radial spokes emanating from a center of mass of said region of interest and said boundary of said region of interest;
      receiving a second image of said region of interest, said second image having been taken at a second time;
      registering said first image with said second image to create a new, third image in which said region of interest in said third image at least approximates a size and shape of said region of interest in said first image, but in which said region of interest in said third image has been repositioned with respect to said region of interest in said first image to reflect a change in orientation of said anatomical structure between said first image and said second image, where registering said first image with said second image comprises:
         identifying at least a particular one of said plurality of volumetric sub-regions of interest within said region of interest in said first image;
         identifying said particular one volumetric sub-region of interest within said region of interest in said second image; and
         mapping said particular one volumetric sub-region of interest in said first image to said particular one volumetric sub-region of interest in said second image; and
      using said second and third images to assess a change in said region of interest between said first time and said second time.

2. The computer system of claim 1, wherein:
   said particular one volumetric sub-region of interest is a first volumetric sub-region of interest; and
   said registering of said first image with said second image comprises:
      identifying a second volumetric sub-region of interest within said region of interest in said first image;
      identifying said second volumetric sub-region of interest within said region of interest in said second image; and
      mapping said second volumetric sub-region of interest in said first image to said second volumetric sub-region of interest in said second image.

3. The computer system of claim 2, wherein said registering of said first image with said second image comprises:
   identifying a plurality of at least three volumetric sub-regions of interest within said region of interest in said first image, said plurality of volumetric sub-regions of interest including said first volumetric sub-region of interest, said second volumetric sub-region of interest, and at least a third volumetric sub-region of interest;
   identifying each of said plurality of at least three volumetric sub-regions of interest within said region of interest in said second image; and
   mapping each of said plurality of at least three volumetric sub-regions of interest in said first image to corresponding ones of said plurality of at least three sub-regions of interest in said second image.

4. The computer system of claim 3, wherein each of said plurality of at least three volumetric sub-regions of interest in said first image is a pie shaped section within said region of interest in said first image.

5. The computer system of claim 4, wherein said plurality of at least three volumetric sub-regions of interest define at least a portion of a surface of said region of interest.

6. The computer system of claim 5, wherein said plurality of at least three volumetric sub-regions of interest substantially define an entire outer surface of said region of interest.

7. The computer system of claim 5, wherein said computer system is configured for tracking said plurality of at least three volumetric sub-regions of interest from said first image to said third image to track changes in a shape of said region of interest.

8. The computer system of claim 1, wherein said region of interest comprises a tumor.

9. The computer system of claim 1, wherein:
   said first time is a time before a patient associated with said region of interest receives a particular treatment designed to affect said region of interest; and
   said second time is a time after said patient receives said particular treatment.

10. The computer system of claim 1, wherein said using said second and third images to assess a change in said region of interest between said first time and said second time comprises using said second and third images to assess a change in metabolic activity within said particular one volumetric sub-region of interest between said first time and said second time.

11. The computer system of claim 1, wherein said using said second and third images to assess a change in said region of interest between said first time and said second time comprises using said second and third images to assess a change in volume of said particular one volumetric sub-region of interest between said first time and said second time.

12. The computer system of claim 11, wherein said computer system is configured for tracking said plurality of volumetric sub-regions of interest from said first image to said third image to track changes in a volume of said region of interest.

13. The computer system of claim 12, wherein said region of interest comprises a tumor.

14. The computer system of claim 1, wherein said first image comprises a PET image.

15. The computer system of claim 1, wherein said registering said first image with said second image to create said third image comprises using rigid registration to register said first image with said second image.

16. The computer system of claim 1, wherein said registering said first image with said second image to create said third image comprises using elastic or deformable registration to register said first image with said second image.

17. A computer system comprising:
   at least one processor; and
   memory, wherein said computer system is configured for:
      receiving a first image of a region of interest, said region of interest comprising a tissue that moves according to repeating movement cycle, said first image being an image of said region of interest at a first point in said repeating movement cycle;

receiving a second image of said region of interest, said second image being an image of said region of interest at a second point in said repeating movement cycle; and registering said first image with said second image to create a new, third image in which said region of interest in said third image at least approximates a size and shape of said region of interest in said first image, but in which said region of interest in said third image has been repositioned with respect to said first image to compensate for movement of said tissue according to said repeating movement cycle, where registering said first image with said second image comprises dividing said region of interest in said first image into a plurality of sub-regions of interest based on a center of mass of said region of interest in said first image and mapping at least one of said plurality of sub-regions of interest in said first image to a corresponding sub-region of interest of said region of interest in said second image.

18. The computer system of claim 17, wherein said registering said first image with said second image comprises:

identifying a plurality of volumetric sub-regions of interest of said plurality of sub-regions of interest within said region of interest in said first image;

identifying each of said plurality of volumetric sub-regions of interest in said second image, said plurality of volumetric sub-regions defined by radial spokes emanating from said center of mass of said region of interest in said first image and a boundary defining said region of interest in said first image; and mapping each of said plurality of volumetric sub-regions of interest in said first image to a corresponding volumetric sub-region of interest of said plurality of volumetric sub-regions of interest in said second image.

19. The computer system of claim 18, wherein each of said plurality of sub-regions of interest in said first image is a pie shaped section within said region of interest in said first image.

20. The computer system of claim 19, wherein said plurality of sub-regions of interest in said first image substantially define an entire outer surface of said region of interest.

21. The computer system of claim 17, wherein said region of interest is a lung.

22. The computer system of claim 17, wherein said region of interest is a heart.

23. The computer system of claim 17, wherein said region of interest comprises a tumor.

24. The computer system of claim 17, wherein said first image comprises a PET image.

25. The computer system of claim 17, wherein said registering said first image with said second image to create said third image comprises using rigid registration to register said first image with said second image.

26. The computer system of claim 17, wherein said registering said first image with said second image to create said third image comprises using elastic or deformable registration to register said first image with said second image.

27. A non-transitory computer-readable medium storing computer executable instructions for performing the steps of:

receiving a first image of a region of interest, said first image having been taken at a first time, and said region of interest being associated with a particular anatomical structure, where a boundary defines said region of interest in said first image;

dividing said region of interest into a plurality of volumetric sub-regions of interest, said plurality of volumetric sub-regions of interest defined based on a center of mass of said region of interest and said boundary defining said region of interest in said first image;

receiving a second image of said region of interest, said second image having been taken at a second time;

registering said first image with said second image to create a new, third image in which said region of interest in said third image at least approximates a size and shape of said region of interest in said first image, but in which said region of interest in said third image has been repositioned with respect to said first image to reflect a change in orientation of said anatomical structure between said first image and said second image, where registering said first image with said second image comprises:

identifying at least a particular one of said plurality of volumetric sub-regions of interest within said region of interest in said first image;

identifying said particular one volumetric sub-region of interest within said region of interest in said second image; and mapping said particular one volumetric sub-region of interest in said first image to said particular one volumetric sub-region of interest in said second image; and using said second and third images to assess a change in said region of interest between said first time and said second time.

28. The computer readable medium of claim 27, wherein:

said particular one volumetric sub-region of interest in said first image is a first volumetric sub-region of interest; and said step of registering said first image with said second image comprises:

identifying a second volumetric sub-region of interest within said region of interest in said first image;

identifying said second volumetric sub-region of interest within said region of interest in said second image; and mapping said second volumetric sub-region of interest in said first image to said second volumetric sub-region of interest in said second image.

29. The computer readable medium of claim 28, wherein said step of registering said first image with said second image comprises:

identifying a plurality of at least three volumetric sub-regions of interest within said region of interest in said first image, said plurality of at least three volumetric sub-regions of interest including said first volumetric sub-region of interest, said second volumetric sub-region of interest, and at least a third volumetric sub-region of interest;

identifying each of said plurality of at least three volumetric sub-regions of interest within said region of interest in said second image; and mapping each of said plurality of at least three volumetric sub-regions of interest in said first image to corresponding ones of said plurality of at least three sub-regions of interest in said second image.

30. The computer readable medium of claim 27, wherein each of said plurality of at least three volumetric sub-regions of interest within said region of interest in said first image is defined by radial spokes emanating from said center of mass of said region of interest and said boundary defining said region of interest in said first image.

\* \* \* \* \*